(12) United States Patent
Wu et al.

(10) Patent No.: US 12,364,439 B2
(45) Date of Patent: Jul. 22, 2025

(54) MODULATION MODEL OF PHOTOPLETHYSMOGRAPHY SIGNAL FOR VITAL SIGN EXTRACTION

(71) Applicants: UNIVERSITY OF MARYLAND, COLLEGE PARK, College Park, MD (US); United States of America, as Represented by the Secretary, Department of Health and Human Services, Washington, DC (US)

(72) Inventors: Min Wu, Clarksville, MD (US); Mingliang Chen, College Park, MD (US); Qiang Zhu, College Park, MD (US); Quanzeng Wang, Olney, MD (US)

(73) Assignees: UNIVERSITY OF MARYLAND, COLLEGE PARK, College Park, MD (US); UNITED STATES OF AMERICA, AS REPRESENTED BY SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 832 days.

(21) Appl. No.: 17/394,269

(22) Filed: Aug. 4, 2021

(65) Prior Publication Data

US 2022/0039753 A1 Feb. 10, 2022

Related U.S. Application Data

(60) Provisional application No. 63/061,115, filed on Aug. 4, 2020.

(51) Int. Cl.
*A61B 5/00* (2006.01)
*A61B 5/024* (2006.01)
*A61B 5/08* (2006.01)

(52) U.S. Cl.
CPC .......... *A61B 5/7228* (2013.01); *A61B 5/0004* (2013.01); *A61B 5/02416* (2013.01); *A61B 5/0816* (2013.01); *A61B 5/7225* (2013.01)

(58) Field of Classification Search
CPC ........................ A61B 5/02416; A61B 5/0816
See application file for complete search history.

(56) References Cited

U.S. PATENT DOCUMENTS

2006/0258921 A1* 11/2006 Addison ................ A61B 5/742
600/323

OTHER PUBLICATIONS

Riccardo Favilla et al., "Heart Rate and Heart Rate Variability From Single-Channel Vidio and ICA Integration of Multiple Signals", IEEE Journal of Biomedical and Health Informatics, vol. 23, No. 6, Nov. 2019, DOI: 10.1109/JBHI.2018.2880097, 11 pages.

(Continued)

*Primary Examiner* — Tse W Chen
*Assistant Examiner* — Michael A Catina
(74) *Attorney, Agent, or Firm* — ISQUIRE PATTON BOGGS (US) LLP

(57) ABSTRACT

An apparatus for vital sign extraction. The apparatus may receive a vital signal of a subject from a sensing device. The apparatus may also perform a preprocessing procedure on the vital signal via bandpass filtering and normalization to obtain a preprocessed signal. The apparatus may also perform a time-frequency analysis of the preprocessed signal, and estimate a heart rate of the subject from a dominant component of the preprocessed signal by finding location of a maximum spectral energy of the time-frequency analysis. In addition, the apparatus may identify guard components in the preprocessed signal in view of the dominant component, and derive a respiratory rate of the subject from a length of an interval between the dominant component and each of the guard components.

11 Claims, 9 Drawing Sheets

(56) References Cited

OTHER PUBLICATIONS

Jerome Gilles, "Empirical Wavelet Transform", IEEE Transactions on Signal Processing, vol. 61, No. 16, Aug. 15, 2013, DOI: 10.1109/TSP.2013.2265222, 12 pages.

A. Garde et al., "Empirical Mode Decomposition for Respiratory and Heart Rate Estimation from the Photoplethysmogram", Computing in Cardiology 2013; 40:799-782, 4 pages.

Qiang Zhu et al., "Adaptive Multi-Trace Carving for Robust Frequency Tracking in Forensic Applications", IEEE Transactions on Information Forensics and Security, vol. 16, 2021, https://www.ieee.org/publications/rights/index.html, 16 pages.

Qiang Zhu et al., "Adaptive Multi-Trace Carving Based on Dynamic Programming", Asilomar 2018, 5 pages.

Walter Karlen et al., "Multiparameter Respiratory Rate Estimation From the Photoplethysmogram", IEEE Transactions on Biomedical Engineering, vol. 60, No. 7, Jul. 2013, DOI: 10.1109/TBME.2013.2246160, 8 pages.

Kirk Shelley, "Photoplethysmography: Beyond the Calculation of Arterial Oxygen Saturation and Heart Rate", DOI: 10:1213/01.ane.0000269512.82836.c9, 6 pages.

Mingliang Chen et al., "Respiratory Rate Estimation from Face Videos", 4 pages.

Drew A. Birrenkott et al., "Robust Estimation of Respiratory Rate via ECG- and PPG-Derived Respiratory Quality Indices", 4 pages.

Jesus Lazaro et al., "Deriving respiration from photoplethysmographic pulse width", Medical Biological Engineering and Computing (2013) 51:233-242, 10 pages.

\* cited by examiner

MODULATION MODEL OF PHOTOPLETHYSMOGRAPHY SIGNAL FOR VITAL SIGN EXTRACTION

CROSS-REFERENCE TO RELATED APPLICATION

This application claims priority to U.S. provisional patent application No. 63/061,115 filed on Aug. 4, 2020. The contents of this earlier filed application are hereby incorporated by reference herein in their entirety.

FIELD

Some example embodiments may generally relate to vital sign monitoring from sensing data, and monitoring and diagnosing diseases related to cardiovascular and lung functions. For example, certain example embodiments may relate to apparatuses, systems, and/or methods for modulating a model of photoplethysmography (PPG) signals for vital sign extraction.

BACKGROUND

Monitoring vital signs, such as heart rate (HR) and respiratory rate (RR) can be essential when analyzing a patient's physiological condition, and monitoring and diagnosing diseases related to cardiovascular and lung functions. While electrocardiography (ECG) has often been the standard to study a patient's cardiovascular conditions, the portability, complexity, and cost of ECG equipment limit its use in health care, especially in-home care. Finding a feasible approach to track multiple vital signs from a simple, accessible, and easy-to-use sensor is desirable in daily health monitoring, especially in emerging mobile health (mHealth) care.

PPG is a technique that can be used in clinical settings to capture vital signs by detecting blood content and volume changes in the microvascular bed of tissue. PPG has been proven to be feasible in extracting such vital signs as HR and RR from the PPG signal. However, the signal generally has weak traces of respiration information, limiting the accuracy of RR estimation. Thus, there is a need for improved PPG signal analysis technologies to obtain accurate vital sign information/features from the PPG spectrum.

SUMMARY

Some example embodiments may be directed to a method. The method may include receiving a vital signal of a subject from a sensing device. The method may also include performing a preprocessing procedure on the vital signal via bandpass filtering and normalization to obtain a preprocessed signal. The method may further include performing a time-frequency analysis of the preprocessed signal. In addition, the method may include estimating a HR of the subject from a dominant component of the preprocessed signal by finding the location of a maximum spectral energy of the time-frequency analysis. Further, the method may include identifying guard components in the preprocessed signal with respect to the dominant component. The method may also include deriving a RR of the subject from a length of an interval between the dominant component and each of the guard components.

Other example embodiments may be directed to an apparatus. The apparatus may include at least one processor and at least one memory including computer program code. The at least one memory and computer program code may be configured to, with the at least one processor, cause the apparatus at least to receive a vital signal of a subject from a sensing device. The apparatus may also be caused to perform a preprocessing procedure on the vital signal via bandpass filtering and normalization to obtain a preprocessed signal. The apparatus may further be caused to perform a time-frequency analysis of the preprocessed signal. In addition, the apparatus may be caused to estimate a HR of the subject from a dominant component of the preprocessed signal by finding the location of a maximum spectral energy of the time-frequency analysis. Further, the apparatus may be caused to identify guard components in the preprocessed signal with respect to the dominant component. The apparatus may also be caused to derive a RR of the subject from a length of an interval between the dominant component and each of the guard components.

Other example embodiments may be directed to an apparatus. The apparatus may include means for receiving a vital signal of a subject from a sensing device. The apparatus may also include means for performing a preprocessing procedure on the vital signal via bandpass filtering and normalization to obtain a preprocessed signal. The apparatus may further include means for performing a time-frequency analysis of the preprocessed signal. In addition, the apparatus may include means for estimating a HR of the subject from a dominant component of the preprocessed signal by finding the location of a maximum spectral energy of the time-frequency analysis. Further, the apparatus may include means for identifying guard components in the preprocessed signal with respect to the dominant component. The apparatus may also include means for deriving a RR of the subject from a length of an interval between the dominant component and each of the guard components.

In accordance with other example embodiments, a non-transitory computer-readable medium may be encoded with instructions that may, when executed in one or more machines or one or more hardware devices, perform a method. The method may include receiving a vital signal of a subject from a sensing device. The method may also include performing a preprocessing procedure on the vital signal via bandpass filtering and normalization to obtain a preprocessed signal. The method may further include performing a time-frequency analysis of the preprocessed signal. In addition, the method may include estimating a HR of the subject from a dominant component of the preprocessed signal by finding the location of a maximum spectral energy of the time-frequency analysis. Further, the method may include identifying guard components in the preprocessed signal with respect to the dominant component. The method may also include deriving a RR of the subject from a length of an interval between the dominant component and each of the guard components.

Other example embodiments may be directed to a computer program product that performs a method. The method may include receiving a vital signal of a subject from a sensing device. The method may also include performing a preprocessing procedure on the vital signal via bandpass filtering and normalization to obtain a preprocessed signal. The method may further include performing a time-frequency analysis of the preprocessed signal. In addition, the method may include estimating a HR of the subject from a dominant component of the preprocessed signal by finding the location of a maximum spectral energy of the time-frequency analysis. Further, the method may include identifying guard components in the preprocessed signal with respect to the dominant component. The method may also include deriving a RR of the subject from a length of an interval between the dominant component and each of the guard components.

BRIEF DESCRIPTION OF THE DRAWINGS

For a proper understanding of example embodiments, reference should be made to the accompanying drawings, wherein.

DETAILED DESCRIPTION

It will be readily understood that the components of certain example embodiments, as generally described and illustrated in the figures herein, may be arranged and designed in a wide variety of different configurations. The following is a detailed description of some example embodiments of systems, methods, apparatuses, and computer program products for modulating a model of PPG signals for vital sign extraction.

The features, structures, or characteristics of example embodiments described throughout this specification may be combined in any suitable manner in one or more example embodiments. For example, the usage of the phrases "certain embodiments," "an example embodiment," "some embodiments," or other similar language, throughout this specification refers to the fact that a particular feature, structure, or characteristic described in connection with an embodiment may be included in at least one embodiment. Thus, appearances of the phrases "in certain embodiments," "an example embodiment," "in some embodiments," "in other embodiments," or other similar language, throughout this specification do not necessarily refer to the same group of embodiments, and the described features, structures, or characteristics may be combined in any suitable manner in one or more example embodiments.

Additionally, if desired, the different functions or steps discussed below may be performed in a different order and/or concurrently with each other. Furthermore, if desired, one or more of the described functions or steps may be optional or may be combined. As such, the following description should be considered as merely illustrative of the principles and teachings of certain embodiments, and not in limitation thereof.

Figure 1:
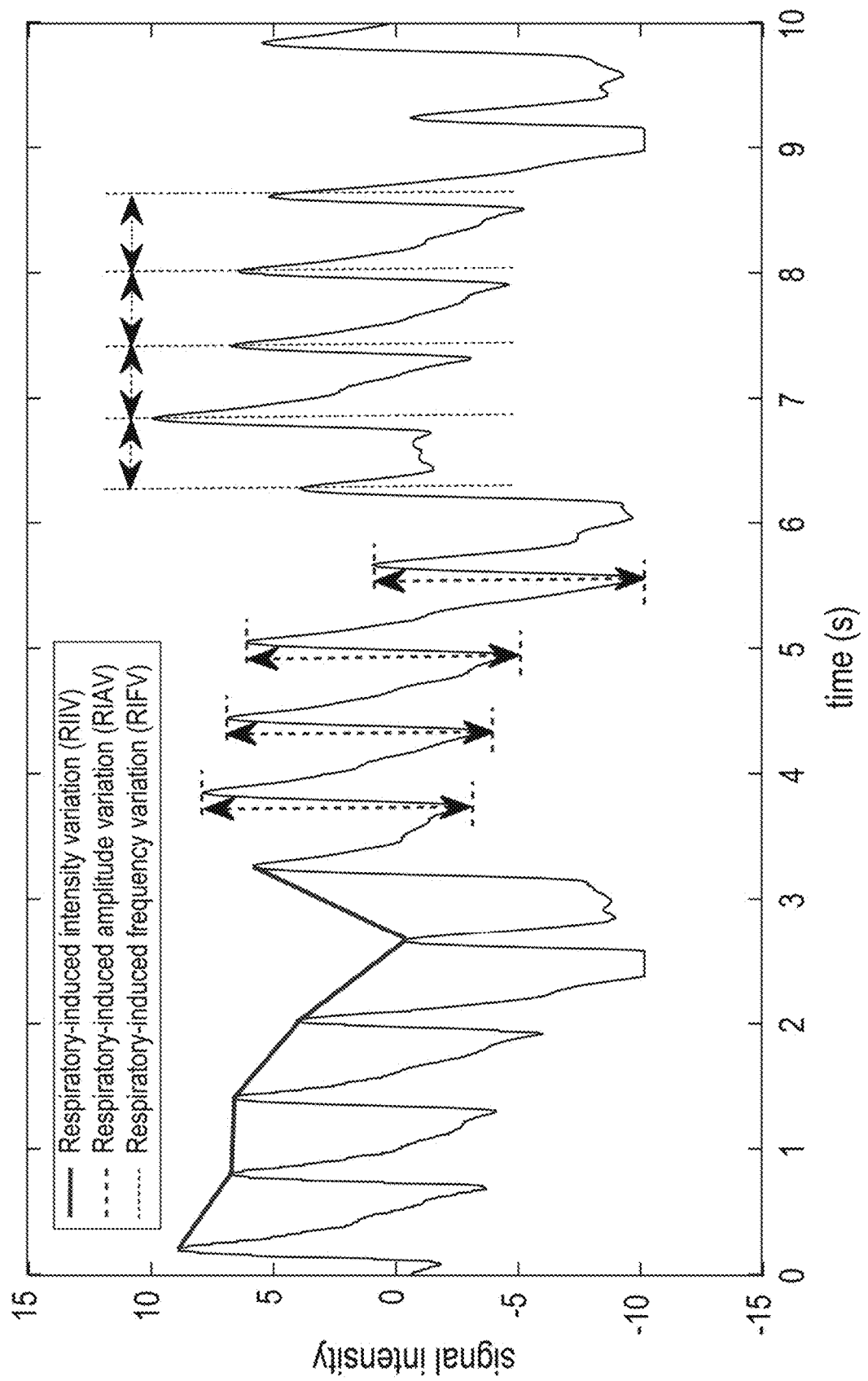
FIG. 1 illustrates an example of three types of respiratory-induced variations in a PPG signal.

Respiration may have several effects on PPG signals. For example, a change in intrathoracic pressure leads to blood exchange between the pulmonary and systemic circulations, resulting in a change in the perfusion baseline during breathing cycles, which is referred to as respiratory-induced intensity variation (RIIV). A second effect may include respiratory-induced amplitude variation (RIAV). RIAV is characterized by a change in ventricular filling, which may lead to a corresponding change in cardiac output, which represents the change in peripheral pulse strength during breathing RIAV suggests that the PPG signal is subject to amplitude modulation (AM). A third effect may include an autonomic response to respiration known as respiratory-induced frequency variation (RIFV), indicating that the PPG signal can be subject to frequency modulation (FM). In this case, the instantaneous HR may vary to synchronize with the respiratory cycle—the HR increases during inspiration and decreases during expiration. FIG. 1 illustrates an example of these respiratory-induced effects. Beyond RIIV, RIAV, and RIFV, other respiratory-induced variations in the PPG signal have been considered to estimate RR, such as a pulse amplitude variability, and a pulse width variability.

Considering the combined effect of RIIV, RIAV, and RIFV, time-domain approaches have been considered to improve the accuracy of RR estimation. The three respiratory-induced variations may be extracted from the PPG signal in the time domain and used individually to produce three separate RR estimates. Averaging fusion or auto-regression (AR) fusion may then be employed to combine the three RR estimates and produce the final RR estimate. The fusion strategies demonstrated an improvement of more than 1 breath per minute (BrPM) in the root mean square error (RMSE), compared with the estimates obtained from using RIIV, RIAV, and RIFV individually. Since these approaches need to examine the valley and peak points in PPG signals to extract the three types of respiratory-induced information, they can be sensitive to additive noise. Thus, to obtain accurate features in the time domain, these approaches may generally need a high data sampling rate. In addition, auto-regressive modeling and Gaussian processes may be used to explore the respiratory-induced variations in PPG signals.

PPG signals have also been investigated in the frequency domain. In the frequency domain, the RIIV in the PPG signal may be considered with the assumption that the breath-related signal is superimposed onto the pulse signal. That is, the RR can be estimated by observing the lower frequency range of the spectrum (<0.7Hz). A variety of frequency analysis techniques, including periodogram, wavelet decomposition, empirical mode decomposition (EMD), empirical wavelet transforms (EWT), and correntropy spectral density (CSD) have been applied to obtain accurate RR estimates in the normal RR range. However, the superimposition model does not consider RIAV and RIFV. The RIIV factor does not always appear detectable in PPG signals, especially after signal preprocessing operations such as filtering and detrending have been applied to it. Furthermore, the frequency-domain methods have a low median RMSE of 0.9 BrPM, but large variances in the estimation error, indicating that these algorithms are not robust and stable. RIAV and RIFV may be in PPG signals via the variable frequency complex demodulation method (VFCDM), which is a general frequency analysis framework used to estimate variable frequency. However, compared with the frequency-domain methods using RIIV, the VFCDM has a smaller variance in estimation error but larger median error (about 2.5 breaths/min).

In some cases, PPG signals may be collected by a pulse oximeter attached to the skin of a subject (e.g., human), which may be referred to as the "contact PPG (cPPG)

signal". In the emerging mHealth care, a newly formed modality of PPG, "remote PPG (rPPG)", has garnered growing interest since the rPPG signal may be captured from a color video of the subject's face.

Under the principle of rPPG, the blood volume may change under the skin and influence the intensity and color of the reflected light from the skin. This pattern is consistent with heartbeat cycles. Although such subtle momentary changes in the reflected light from the facial skin are not detectable by the human eye, they can be captured by a color camera. Using an accessible color camera to collect PPG signals, the rPPG technique can be convenient and user-friendly, freeing users of contact sensors. However, the rPPG technique may result in low signal-to-noise ratio (SNR). Since a color camera is normally one-half to one meter away from a subject's skin, non-ideal illumination conditions and the subject's voluntary movements can influence the signal quality. Although effective de-noising operations have been employed to deal with realistic conditions and improve HR estimation accuracy from the rPPG signal, the research in RR estimation from such signal is still limited, and RR has mainly been estimated via HR variability (HRV) extraction in the time domain.

Figure 2:
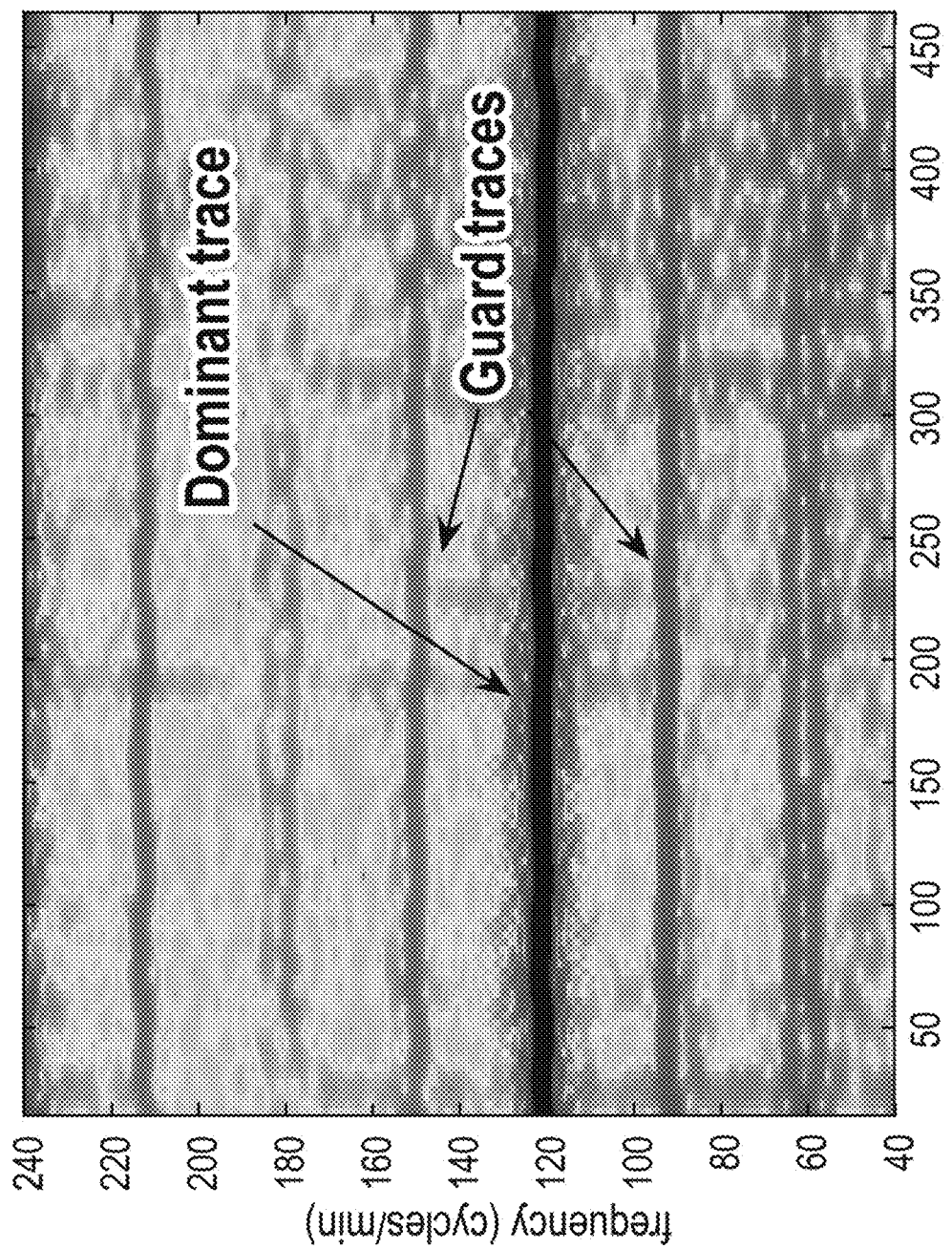
FIG. 2 illustrates an example spectrogram of a subject's PPG signal, according to certain embodiments.

To improve the PPG signal analysis technology, certain embodiments provide a frequency-domain method based on a modulation model to extract RIAV and RIFV features from the PPG spectrum and to estimate HR and RR. FIG. 2 illustrates an example spectrogram, according to certain embodiments. In particular, FIG. 2 illustrates a spectrogram of a subject's PPG signal, according to certain embodiments. As illustrated in FIG. 2, a dominant frequency trace, and two guard traces on both sides of the dominant trace can be identified. In certain embodiments, the spectrograms (i.e., time-frequency representations) may be presented to show the variation of the vital signs with time. Further, certain embodiments may model PPG signals using amplitude and frequency modulation (AM-FM), and apply it to HR and RR estimation. As such, the AM-FM method may utilize relatively robust respiration-induced variation features, avoids the drawbacks of the peak/valley detection algorithms (i.e., detecting peak and valley points in PPG signals) under noisy or low-sampling rate scenarios, and improves the accuracy and robustness of RR estimation from PPG signals.

As discussed herein, certain embodiments may provide an AM-FM modulation model for PPG signals. This model may explain the dominant and guard traces in a PPG spectrogram, as illustrated in FIG. 2. Certain embodiments may also provide a robust frequency-domain method based on the AM-FM model for HR and RR extraction from the PPG spectra, and take advantage of the symmetry of the dominant and guard traces. Additionally, certain embodiments may provide a means of validating the AM-FM method on both the cPPG and the rPPG signals in terms of accuracy and robustness.

Figure 3:
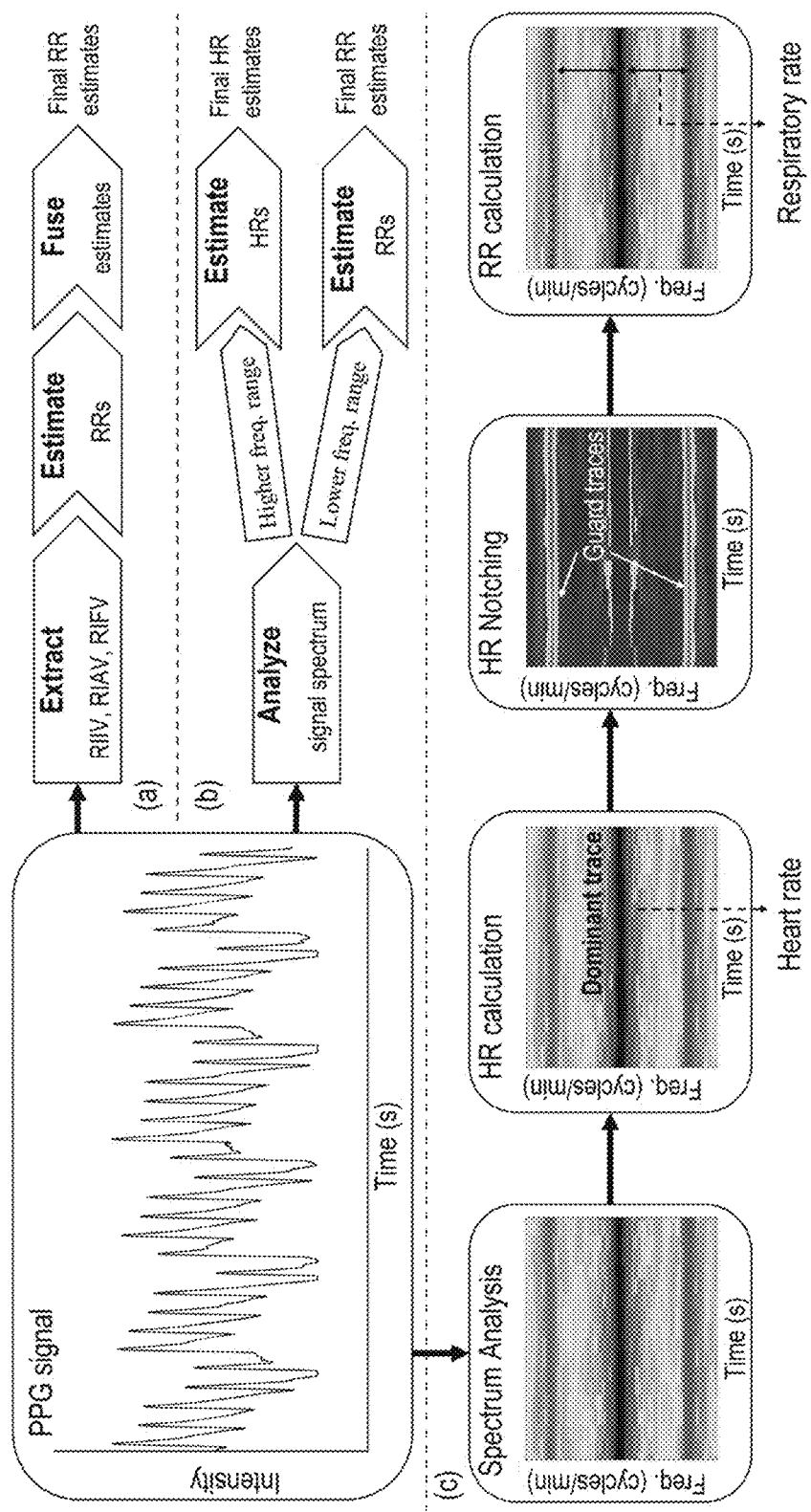
FIG. 3 illustrates an example pipeline of an amplitude and frequency modulation (AM-FM) method, according to certain embodiments.

Based on the observation of the spectrogram illustrated in FIG. 2, certain embodiments may provide a frequency-domain method to extract the three traces from the spectrogram to infer the HR and RR. FIG. 3 illustrates an example pipeline of the AM-FM method, according to certain embodiments. Part (a) of FIG. 3 illustrates typical components of RR estimation via a time-domain, and part (b) of FIG. 3 illustrates frequency-domain approaches. According to certain embodiments, the pipeline of the time-domain methods may include extracting respiratory-induced variation features in the time-domain, estimating an individual RR from each variation feature, and fusing the estimated RRs to produce the final result. Additionally, the pipeline of the frequency-domain methods may include estimating the spectrum of the PPG signal and extracting HR and RR from different frequency ranges of interest. As illustrated in part (c) of FIG. 3, the pipeline of the AM-FM method may apply spectrum analysis to the PPG signal, where three main frequency traces can be observed. For instance, the spectrum analysis may include performing an analysis of the signal in the frequency domain, and performing the spectrum analysis of the pre-processed signal may give rise to the spectrogram illustrated in FIG. 2. According to certain embodiments, the dominant frequency component—HR—may be extracted from the spectrum. Then, the dominant trace may be adaptively notched, and the two guard traces may be extracted from the residual spectrum. In certain embodiments, the RR may be derived from the frequency distance between the dominant and the guard traces. In the spectrograms, the horizontal and the vertical axes denote time and frequency, respectively, and the frequency range illustrated in FIG. 3 has been cropped from 80 to 160 cycles/min.

As noted herein, respiration may influence the PPG signal in three aspects: RIIV, RIAV, and RIFV. However, RIIV is not a robust variation feature for RR estimation since the baseline shift of the signal may be contaminated. In cPPG cases, high-pass filtering may be performed in the pulse oximeter to remove the slow baseline shift in the cPPG signal. Such built-in filtering may weaken the RIIV effect. Further, in rPPG cases, illumination variation from the external environments may influence the baseline shift. Thus, certain embodiments may just consider RIAV and RIFV in modeling PPG signals. In certain embodiments, under the AM-FM model, the HR and RR signals may be assumed to be purely sinusoidal functions with zero phase in a short time period.

According to certain embodiments, the PPG signal s(t) may be expressed as an AM-FM signal:

$$s(t) = \underbrace{(1 + k_a \sin(2\pi f_{rr} t))}_{AM: s_a(t)} \underbrace{\cos(2\pi f_{hr} t + k_f \sin(2\pi f_{rr} t))}_{FM: s_f(t)}. \quad (1)$$

In equation (1), s(t) may be assumed to have unit amplitude, $f_{hr}$ and $f_{rr}$ denote HR and RR, respectively, and $k_a$ and $k_f$ characterize the variation strength in RIAV and RIFV, respectively. After applying the angle sum identity to the FM part in equation (1), the following equation (2) may be obtained:

$$s_f(t) = \cos(2\pi f_{hr} t)\cos(k_f \sin(2\pi f_{rr} t)) - \sin(2\pi f_{hr} t)\sin(k_f \sin(2\pi f_{rr} t)). \quad (2)$$

In equation (2), $k_f$ is a small positive value in modeling a person's PPG signal, and may be estimated to be between 0.11 to 0.32 from a dataset of cPPG signals. Furthermore, equation (2) may be approximated by equation (3):

$$s_f(t) \approx \cos(2\pi f_{hr} t) - \sin(2\pi f_{hr} t) k_f \sin(2\pi f_{rr} t) \quad (3)$$

By applying the product-to-sum identity, equation (3) may become equation (4):

$$s_f(t) \approx \cos(2\pi f_{hr} t) + \frac{k_f}{2}\cos(2\pi (f_{hr} + f_{rr})t) - \frac{k_f}{2}\cos(2\pi (f_{hr} - f_{rr})t). \quad (4)$$

It is noted that $k_a$ is a small positive value between 0.05 to 0.23. Thus, the term $k_a k_f$ may be ignored after expanding the two terms $s_a(t)$ and $s_f(t)$. Accordingly, equation (1) may be simplified to:

$$s(t) \approx \cos(2\pi f_{hr}t) + \frac{k_f}{2}\cos(2\pi(f_{hr}+f_{rr})t) + \frac{k_a}{2}\sin(2\pi(f_{hr}+f_{rr})t) - \frac{k_f}{2}\cos(2\pi(f_{hr}-f_{rr})t) - \frac{k_a}{2}\sin(2\pi(f_{hr}-f_{rr})t). \quad (5)$$

Equation (5) indicates that there may be three main frequency components in a person's PPG signal: $f_{hr}-f_{rr}$, $f_{hr}$, and $f_{hr}+f_{rr}$ as shown in FIG. 2. The AM-FM model of the PPG signal reveals that the PPG spectrum may include noticeable information of HR and RR, and may be jointly extracted from the spectrum.

According to certain embodiments, $k_a$ and $k_f$ may be estimated. For example, in the signal modulation, the modulation index $k_a$ of an AM signal may be computed as equation (6). Further, for the FM signal $s_f(t)$, the instantaneous frequency (equivalent to RIFV in the respiration contexts) may be computed by.

$$\frac{1}{2\pi} \cdot \frac{\partial \phi(t)}{\partial t} = f_{hr} + k_f f_{rr}\cos(2\pi f_{rr}t),$$

which gives rise to equation (7) for $k_f$.

$$k_a = \frac{u_{a,max} - u_{a,min}}{u_{a,max} + u_{a,min}}, \quad (6)$$

$$k_f = \frac{u_{f,max} - u_{f,min}}{2f_{rr}}, \quad (7)$$

where $u_{a,max}$ and $u_{a,min}$, $u_{f,max}$, and $u_{f,min}$ denote the maximum and minimum of the RIAV and RIFV signal, respectively. In certain embodiments, equations (6) and (7) may be applied to estimate the ranges of $k_a$ and $k_f$ in PPG signals from the cPPG dataset.

In certain embodiments, the dominant component and its two guard components may be estimated from the spectrum of a collected PPG signal. In other embodiments, a moving window may be employed to track the variation of the vital signs. As such, certain embodiments may provide the ability to extend the AM-FM method to continuously track the frequency components in long-term monitoring, for example, by applying an adaptive multi-trace carving (AMTC) algorithm, which can apply an efficient tracking method of frequency traces on spectrograms using dynamic programming.

According to certain embodiments, it may be possible to estimate HR. This may be done, for example, by preprocessing the raw PPG signal using bandpass filtering and normalization. In certain embodiments, the preprocessing of the raw PPG signal may be in the time domain to normalize the amplitude of the signal. The bandwidth of the bandpass filter may be 0.25 Hz to 5 Hz, which contains the normal HR range. The filtering removes noises outside the frequency range of interest, and normalization may be applied using a moving window with the length of one second. According to certain embodiments, to normalize one sample x in the signal, the mean $\mu_x$ and standard deviation $\sigma_x$ in the x-centered one-second moving window may be computed. The normalized sample $\tilde{x}$ may be represented as equation (8):

$$\tilde{x} = \frac{x - \mu_x}{\sigma_x}. \quad (8)$$

After the filtering and normalization, the PPG signal has approximately invariant signal energy per unit time.

In certain embodiments, the HR estimation may also include determining the dominant component of the PPG signal. For instance, for a PPG signal s(t) sampled with sampling interval $\Delta_t$, the power spectral density (PSD) may be estimated through the periodogram as follows:

$$S(f) = \frac{\Delta_t}{N}\left|\sum_{n=0}^{N-1} x_n e^{-j2\pi f \Delta_t n}\right|^2, \quad (9)$$

where $x_n$ denotes the n-th sample of the signal, and N is the total number of samples. Here, the HR $f_{hr}$ may be estimated by finding the location of the highest spectral energy in the spectrum (e.g., the largest value among a group of numbers).

Figure 4:
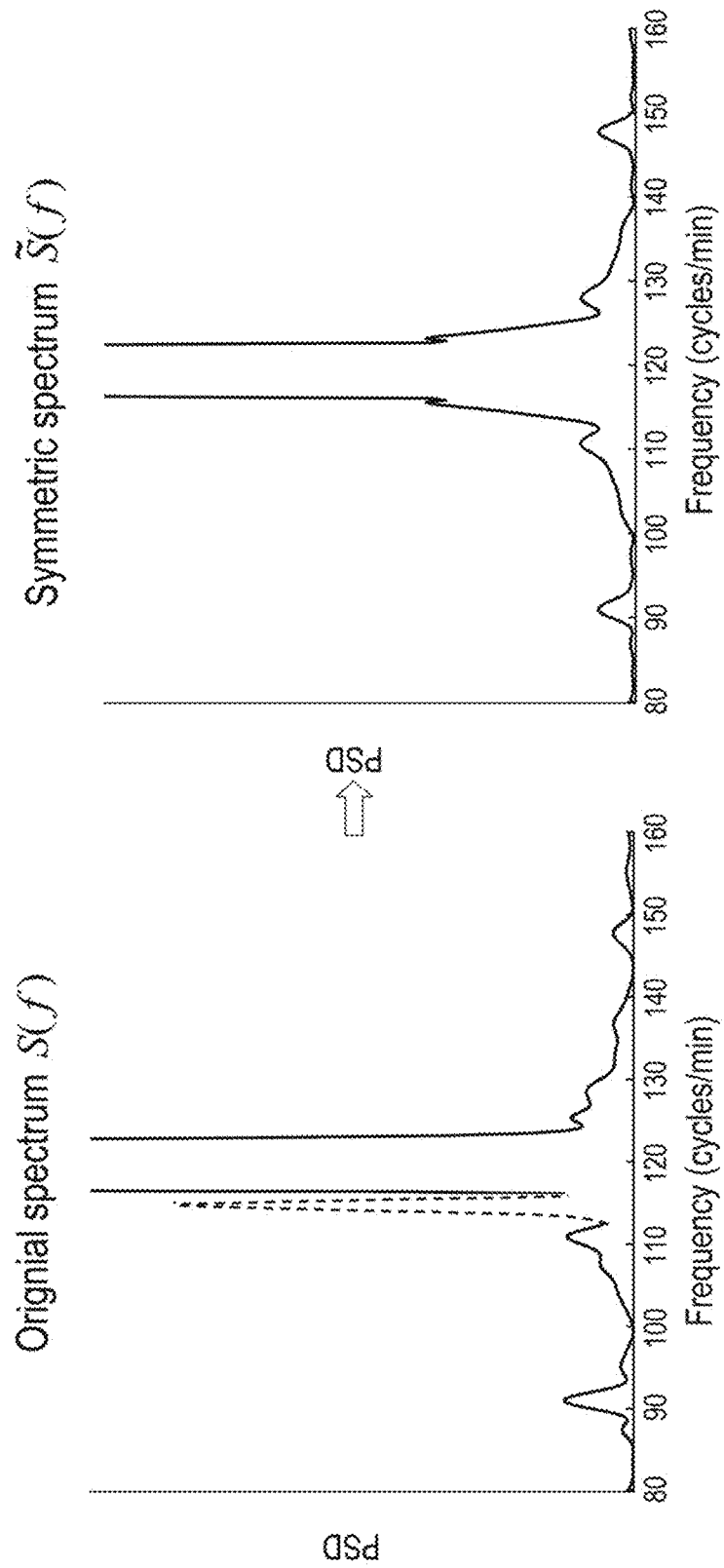
FIG. 4 illustrates an example of symmetrical averaging, according to certain embodiments.

According to certain embodiments, the RR may also be estimated in addition to the HR. For example, in certain embodiments, two guard components, as illustrated in FIG. 2, appear symmetrically on both sides of the dominant component. In certain embodiments, the guard component may be estimated by symmetrical averaging. In particular, to utilize the symmetric property of the two guard components, the spectrum around the dominant component $f_{hr}$ may be flipped around to obtain the symmetric spectrum $\tilde{S}(f)$:

$$\tilde{S}(f) = \sqrt{S(f)S(2f_{hr}-f)}, \quad (10)$$

where $\tilde{S}(f)$ is the flipped spectrum, and $S(f)$ is the original spectrum. By imposing the symmetry property along the dominant peak, a flipping operation may emphasize the symmetric peaks around the dominant peak and eliminates the false alarm of the guard components. FIG. 4 illustrates an example of symmetrical averaging, according to certain embodiments. In particular, FIG. 4 illustrates how the spectrum flipping successfully attenuates the false alarm peaks and protrudes the symmetric guard peaks. As illustrated in FIG. 4, the lower part of the spectra is presented for better visualization of the guard components. Additionally, the false alarm peaks are attenuated by imposing the symmetric property along the dominant peak.

Figure 5:
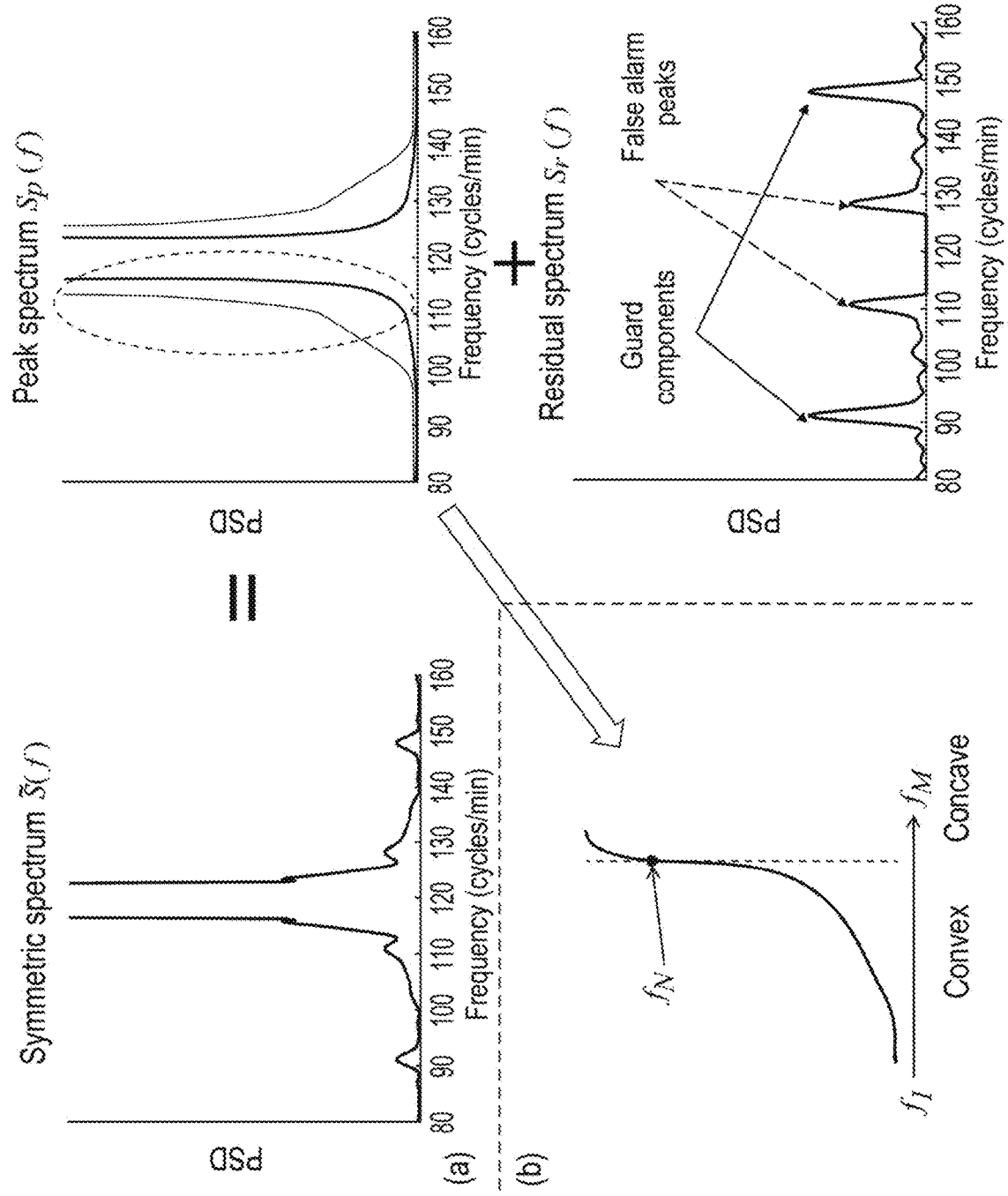
FIG. 5 illustrates an example of energy notching, according to certain embodiments.

In certain embodiments, to estimate the guard peaks, which are lower in intensity than the dominant peak from the symmetric spectrum, the interference of the dominant peak on other small peaks may be reduced by notching its energy. For example, the energy notching step removes the dominant peak's influence on its nearby frequency range and helps mitigate the false alarm peaks lying closely on the slope of the dominant peak. For instance, the notching step may include estimating the shape of the dominant peak using equation (13), and subtracting the shape of the dominant peak from the original spectrum to obtain the residual spectrum. FIG. 5 illustrates energy notching, according to certain embodiments. In particular, as illustrated in FIG. 5, the symmetric spectrum is decomposed into the peak spectrum $S_p(f)$, which contains the dominant component, and the residual spectrum $S_r(f)$, which contains the guard components and false alarm peaks. In part (a) of FIG. 5, symmetric spectrum is the superposition of the peak and the residual spectra. Further, the lower portion of the symmetric and the peak spectra are presented for improved visualization of the guard components. In addition, part (b) of FIG. 5 illustrates the left side of the bell-shaped curve of the peak spectrum, where $f_N$ is the inflection point of the curve slope.

According to certain embodiments, the peak spectrum may be assumed as a bell-like shape. Due to the symmetric property, the left side of the peak spectrum may include as much energy as possible, but may be upper bounded by the spectrum $S(f)$. Further, the left side of the peak spectrum may be characterized as being a non-decreasing function and may include a slope that first increases until the inflection point $f_N$ and then decreases to zero.

In certain embodiments, $\{f_i\}_{i=1,2,\ldots,N,\ldots,M}$ may denote equally sampled frequency values, and $f_N$ denotes the turning point of the curve slope on the left side shown in FIG. 5(b). The left side of the peak spectrum $S_p(f_i)$ is convex before $f_N$, and concave after $f_N$. To find $f_N$, the concavity of each point $f_i$ may be checked, starting from the peak point to the left on the symmetric spectrum, and stopping once reaching the first point that no longer satisfies equation (11):

$$2\tilde{S}(f_i) \geq \tilde{S}(f_{i-}) + \tilde{S}(f_{i+1}), i=M-1, M-2, \quad (11)$$

where $\tilde{S}(f_i)$ denotes the symmetric spectrum. For the concave part where $f_i > f_N$, equation (12) may be obtained as:

$$S_p(f_i) = \tilde{S}(f_i), i=N+1, N+2, \ldots, M \quad (12)$$

According to certain embodiments, for the convex part where $f_i \leq f_N$, the peak spectra may be solved via linear programming expressed in equation (13):

$$\max_{S_p(\cdot)} \sum_{i=1}^{N} S_p(f_i) \quad (13)$$

$$\text{s.t.} \quad S_p(f_{i-1}) \leq S_p(f_i), \quad i = 2, 3, \ldots, N,$$

$$2S_p(f_i) \leq S_p(f_{i-1}) + S_p(f_{i+1}), \quad i = 2, 3, \ldots, N-1,$$

$$0 \leq S_p(f_i) \leq \tilde{S}(f_i), \quad i = 1, 2, \ldots, N.$$

As shown in equation (13), the first inequality enforces the non-decreasing property, and the second inequality enforces the property of convexity. Further, the third inequality sets the upper and the lower bounds. Additionally, in other embodiments, the residual spectrum $S_r(f)$ may be obtained by notching the speak spectrum $S_p(f)$ from the symmetric spectrum $\tilde{S}(f)$, as shown in equation (14):

$$S_r(f) = \tilde{S}(f) - S_p(f). \quad (14)$$

In certain embodiments, after obtaining the residual spectrum, the guard components may be determined. For example, after obtaining the residual spectrum, the locations of the highest spectral energy on both sides of the dominant peak in the residual spectrum may be selected as the guard components. Further, the RR may be derived from the length of the interval between the dominant and guard components.

The effectiveness of the AM-FM method of certain embodiments on two PPG signal datasets has been demonstrated. The PPG signal datasets include a cPPG dataset collected with a contact oximeter and an rPPG dataset captured with a color camera. Due to the distance between human skin and the sensor, and the subject's voluntary movements, the rPPG signal may be noisier than the cPPG signal. To evaluate the AM-FM method, certain embodiments may use a moving window to extract the RR from the PPG signal throughout its duration. The performance of RR estimation algorithms may be assessed using the RMSE metric as shown in equation (15):

$$RMSE = \sqrt{\frac{1}{N}\sum_{i=1}^{n}(x_i^{true} - x_i^{est})^2}, \quad (15)$$

where n is the total number of RR estimates calculated in one PPG signal, and $x_i^{true}$ and $x_i^{est}$ are the ground truth and estimated RR in the i-th window, respectively. In certain embodiments, the Pearson correlation coefficient (PCC) may be computed to measure the linear correlation between the ground truth and estimated RR, and the PCC may range from −1 to 1. The coefficient values −1, 0, and 1 indicate perfect negative linear correlation, no linear correlation, and perfect positive linear correlation between two variables, respectively. In certain embodiments, the evaluation resulted in a PCC value closer to 1, which means a better performance of a method in RR estimations.

The results from conventional works were compared with the results obtained from the AM-FM method of certain embodiments. The comparisons included results from the SmartFusion and CSD methods, ARFusion, EMD, EWT, VFCDM, and HRV-based methods. As will be discussed herein, the SmartFusion and ARFusion methods first extract the three respiratory-induced variation signals in the time domain. SmartFusion estimates three RR values from the three signals and then obtains the final result by averaging the three RR estimates. ARFusion models the three signals via AR modeling and derives the final estimate by fusing the AR spectra of the three respiratory-induced variations with several model orders. In the rPPG case, the HRV-based method only extracts the RIFV feature for RR estimation since RIIV and RIAV are usually attenuated when face videos are captured from a distance. In the frequency-domain methods, frequency analysis techniques—EMD, EWT, and CSD—were employed, respectively, to analyze the frequency components of the PPG signal, and extract the RR from the expected RR frequency range. VFCDM analyzes the PPG signal with spectral estimation and identifies AM and FM dynamics in the signal, which contain RR information.

In certain embodiments, the cPPG dataset was collected with a contact oximeter. Here, the cPPG dataset used included eight-minute cPPG signals of 20 pediatric and 13 adult subjects, during elective surgery and routine anesthesia. The dataset did not disclose the subjects' health status. Further, the PPG signals were collected with an oximeter, and the ground truth RR was obtained from capnography with a sampling rate of 300 Hz.

In the experiments, the length of the moving window was set to 32 seconds in all the methods, except 120 seconds in the CSD method, and the window proceeded for 3 seconds between adjacent estimates. In the method of certain embodiments, the collected signal was downsampled from 300 Hz to 30 Hz to reduce the computational complexity. Downsampling also revealed that the method of certain embodiments can be used for PPG signals collected with a low sampling rate. As discussed herein, the method of certain embodiments was compared with the time-domain methods, SmartFusion and ARFusion, and frequency-domain methods, EMD, EWT, CSD, and VFCDM.

According to certain embodiments, noise was zeroed out in the input cPPG signal, and the RR was estimated on the non-artifact duration of the signal. Further, it was noted that SmartFusion may discard additional RR estimates due to its signal quality assessment strategy. For a fair comparison, the discarded estimates were recovered from SmartFusion by their nearest trustworthy neighbors.

Figure 6:
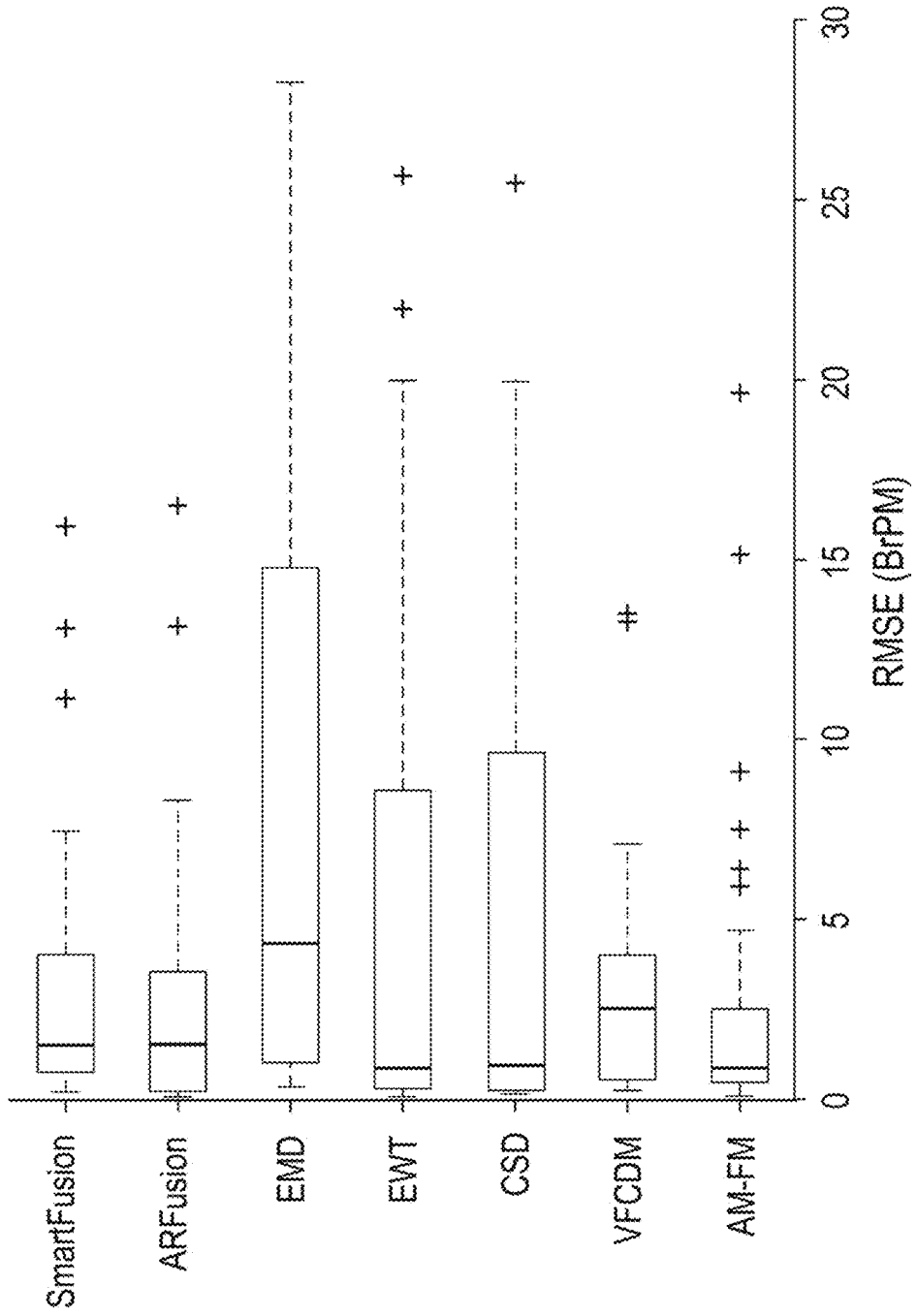
FIG. 6 illustrates a boxplot comparison of root mean square error (RMSE) for RR estimation methods, according to certain embodiments.

FIG. 6 illustrates a boxplot comparison of RMSE for RR estimation methods on the cPPG dataset, according to certain embodiments. In particular, the boxplot shows distributions of RMSEs, with the first (Q1), second (median), and third quartile (Q3) values displayed as left, middle, and right vertical lines of the boxes. Whiskers represent the most extreme values with 1.5 times of the interquartile range (i.e., the range between Q1 and Q3). In addition, the outliers beyond the whiskers are displayed as crosses.

Table 1 below summarizes the quantitative evaluation of the performances of each method, where the best indices are shown in bold. As shown in FIG. 6, SmartFusion and ARFusion have similar performances in RMSE. EMD has the largest median RMSE and variance, and EWT and CSD have smaller median RMSEs, but larger variances in RMSE than SmartFusion and ARFusion. This larger variance indicates that these algorithms are less robust. Further, it can be seen that VFCDM has a similar RMSE variance but a larger mean and median RMSE, compared to SmartFusion and ARFusion. The AM-FM method of certain embodiments has the smallest RMSE median and variance values, indicating that it is the most accurate and robust among these algorithms. Table 1 also shows that the RMSE mean of the AM-FM method is 0.39, 0.14, 3.15, 1.40, 1.33, and 0.46 BrPM lower than the RMSE means of SmartFusion, ARFusion, EMD, EWT, CSD, and VFCDM, respectively. It can also be seen from the RMSE statistics that the AM-FM method has a noticeable reduction in both the median and mean RMSE values and provides the most accurate RR estimates, compared with the other methods. In addition, the PCC index suggests that the proposed method ($\rho$=0.66) has the best positive correlation with the ground truth RR.

TABLE 1

Overall performance of RR estimation methods on cPPG dataset (RMSE Unit: BrPM)

| Method | RMSE statistics Median (Q1, Q3) | Mean | p-value | PCC |
|---|---|---|---|---|
| SmartFusion 4 | 1.53 (0.78, 4.04) | 2.92 | ref. | 0.64 |
| ARFusion 10 | 1.61 (0.31, 3.63) | 2.67 | 0.48 | 0.65 |
| EMD 15 | 4.36 (1.11, 14.6) | 5.68 | 5.7e−4 | 0.45 |
| EWT 16 | 0.90 (0.32, 7.59) | 3.93 | 0.85 | 0.53 |
| CSD 18 | 0.95 (0.27, 6.20) | 3.86 | n/a | n/a |
| VFCDM 19 | 2.55 (0.57, 3.88) | 2.99 | 0.19 | 0.60 |
| AM-FM | 0.89 (0.50, 2.54) | 2.53 | 3.2e−3 | 0.66 |

According to certain embodiments, the Wilcoxon sign rank test was performed to show the differences between these methods, with the SmartFusion method as the reference. The test is a nonparametric test that evaluates whether the group mean ranks differ from two non-normally distributed data groups when the observations are paired. The test results indicate that the AM-FM method (p=3.2×10$^{-3}$) is significantly different from the SmartFusion method.

In certain embodiments, the rPPG dataset may be captured by a color camera. For instance, according to some embodiments, the HRV-based, EMD, EWT, and methods on a self-collected rPPG dataset may be evaluated. The dataset may include 60 one-minute face video clips of 12 subjects with ages ranging from 18 to 50 years old. The skin tones of the participants may generally be categorized into three skin types based on the Fitzpatrick scale: western European (skin type I and II); eastern Asian (skin type III and IV); and African/southern Asian (skin type V and VI). During the recordings, the subjects were asked to sit in front of a desk, where a regular 1080 p webcam was used to capture videos of the frontal positions of subjects' faces at a frame rate of 30 Hz. The ground truth RR was simultaneously measured via a piezo respiratory belt transducer. The transducer was connected to an acquisition system for signal collection with a sampling rate of 500 Hz. The subjects' faces were illuminated by the dedicated fluorescent lights from the ceiling, with a total illuminance of approximately 200 lux. In addition, the subjects' voluntary rigid head motions and non-rigid face motions were allowed during the recording, including talking and facial expressions. Beyond the rPPG videos and the corresponding ground truth RR, information related to subjects' health status was not collected.

For a fair comparison of the RR estimation methods, the rPPG signal was processed in the same way for each method, and a robust extraction algorithm was deployed to extract the pulse signal from the videos. An SSD-ResNet based face detector was first applied to localize the face region in each frame. Then, the region of interest (ROI), defined by the entire face region, was obtained and refined with the face landmark detector and the ROI selection principles. A spatially averaged RGB color signal was then extracted over the detected ROI in each frame. Finally, the pulse signal was computed with the POS algorithm by mapping the 3-channel RGB signal to a 1-channel rPPG signal. After obtaining the rPPG signal, the AM-FM method was applied to estimate the RR and compared with the time-domain HRV-based method and frequency-domain methods, EMD and EWT. The HRV-based method extracted the RIFV signal from the rPPG signal since RIIV and RIAV are usually attenuated during signal preprocessing. Additionally, the EMD and EWT were executed in the same way as in the cPPG case. In RR estimation, the window length was set to 32 seconds and the moving window proceeded one second between adjacent estimates.

Figure 7:
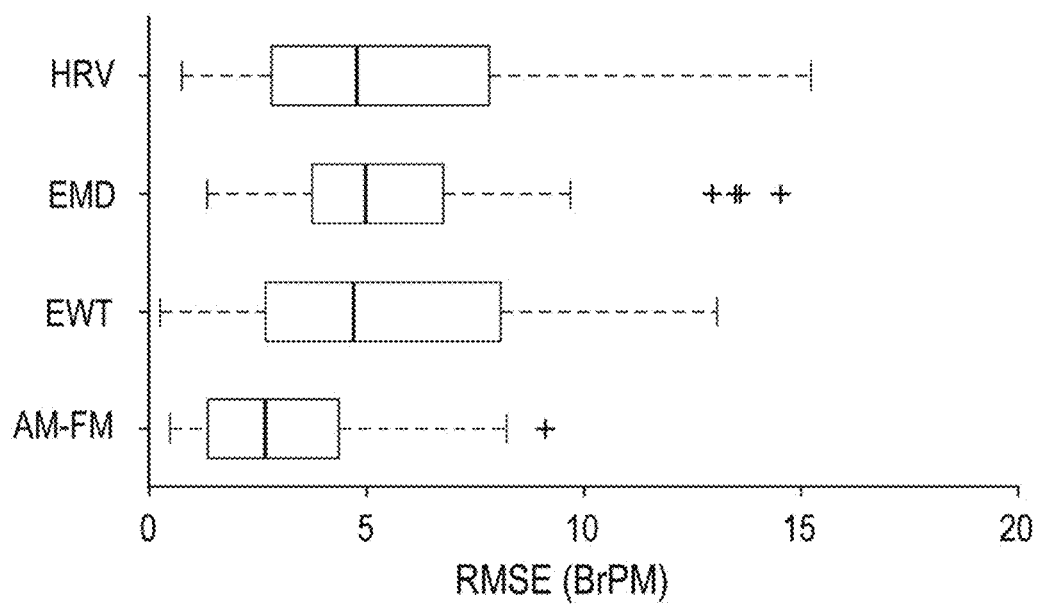
FIG. 7 illustrates another comparison of RMSE for RR estimation methods, according to certain embodiments.

FIG. 7 illustrates a comparison of RMSE for RR estimation methods on the self-collected rPPG dataset, according to certain embodiments. In particular, FIG. 7 illustrates boxplots of the RMSE values associated with the four methods for RR estimation, showing that the AM-FM method has the smallest estimation error among the methods. Table 2 below summarizes the performance statistics of the methods on the rPPG video dataset, where the best values are in bold. As expected, the RR estimation error of the rPPG signal, in general, was larger than that of the cPPG signal (Table 1), since the rPPG signal can be contaminated by noise from a variety of sources, such as voluntary motion and illumination variation. From Table 2, it can be seen that EMD and EWT have the largest error, indicating that RIIV is not a robust feature in the rPPG case. on the other hand, the HRV-based method performs slightly better than EMD and EWT. Overall, the AM-FM method achieved the best performance in terms of median RMSE (2.46 BrPM) and PCC ($\rho$=0.36) with the ground truth RR. In the Wilcoxon sign rank test, the p-value of 6.4×10$^{-4}$ showed that the performance of the AM-FM method is significantly different from the HRV-based method. In the rPPG case, it can be seen that the proposed AM-FM method is the most resistant to noise compared with the other methods.

TABLE 2

Overall performance of RR estimation methods on rPPG Dataset (RMSE Unit: BrPM)

| Method | RMSE statistics | | | |
|---|---|---|---|---|
| | Median (Q1, Q3) | Mean | p-value | PCC |
| HRV 29 | 4.10 (2.73, 7.64) | 5.24 | ref. | 0.32 |
| EMD 15 | 4.99 (3.83, 6.62) | 5.71 | 0.77 | 0.25 |
| EWT 16 | 4.71 (2.92, 8.03) | 5.33 | 0.85 | 0.29 |
| AM-FM | 2.46 (1.29, 4.08) | 3.08 | 6.4e−4 | 0.36 |

Figure 8:
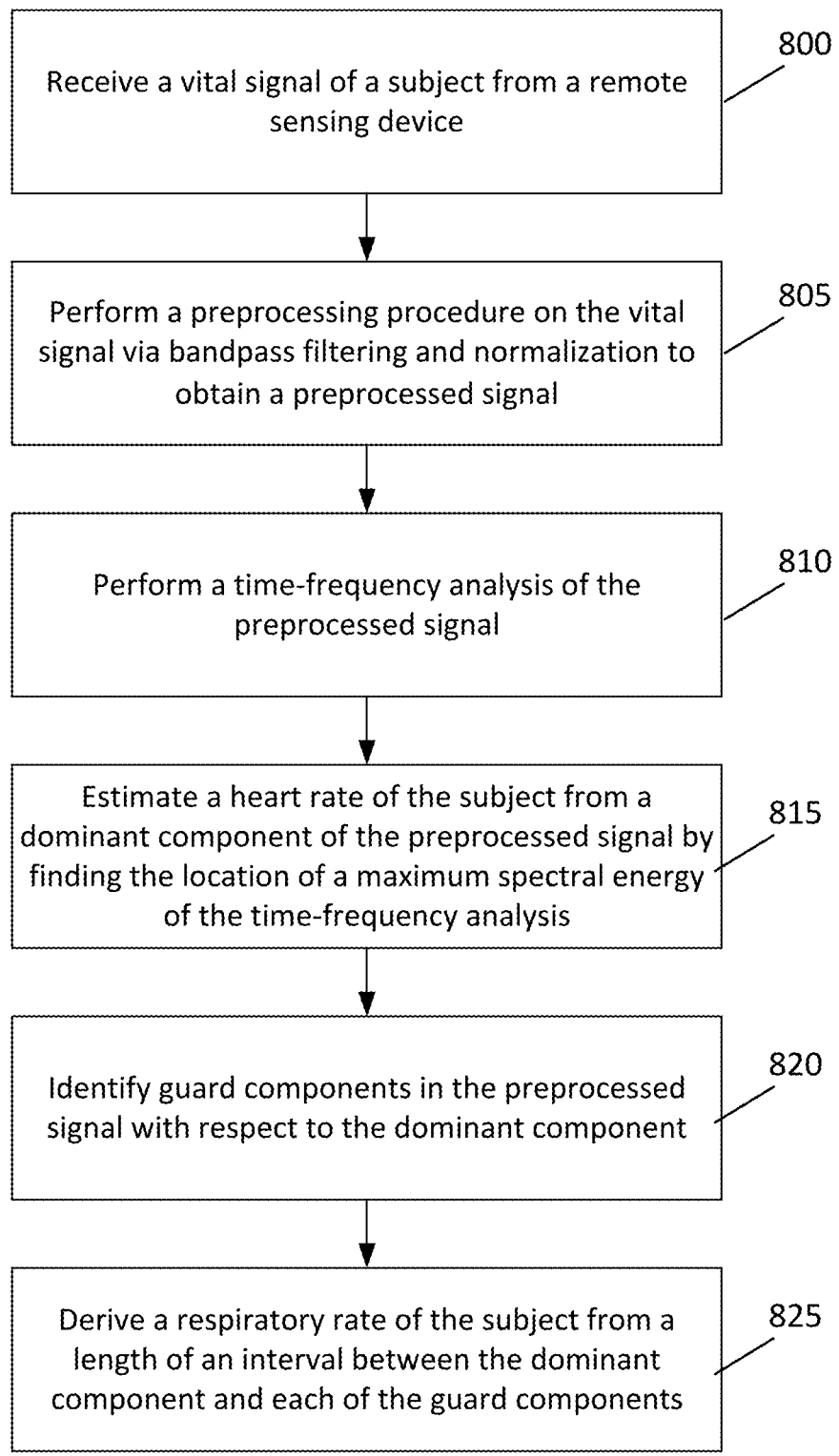
FIG. 8 illustrates an example flow diagram of a method, according to certain embodiments.

FIG. 8 illustrates an example flow diagram of a method, according to certain example embodiments. In certain example embodiments, the flow diagram of FIG. 8 may be performed by a system that includes one or more of a computer apparatus, computer system, network, neural network, apparatus, communication device, mobile computer, mobile communication device, medical device, or other similar device(s). According to certain embodiments, each of these apparatuses of the system may be represented by, for example, an apparatus similar to apparatus 10 illustrated in FIG. 9.

According to one example embodiment, the method of FIG. 8 may include, at 800, receiving a vital signal of a subject from a remote sensing device. In certain embodiments, the vital signal may be a PPG signal, and the remote sensing device may be a wearable computer or communication device, mobile computer, communication device, or medical device that operates individually or together in a computer system or computer network system. At 805, the method may include performing a preprocessing procedure on the vital signal via bandpass filtering and normalization to obtain a preprocessed signal. At 810, the method may include performing a time-frequency analysis of the preprocessed signal. At 815, the method may include estimating a HR of the subject from a dominant component of the preprocessed signal by finding the location of a maximum spectral energy of the time-frequency analysis. At 820, the method may include identifying guard components in the preprocessed signal with respect to the dominant component. At 825, the method may include deriving a RR of the subject from a length of an interval between the dominant component and each of the guard components.

According to certain embodiments, the method may further include applying a symmetric averaging to the preprocessed signal to obtain a symmetric spectrum, decomposing the symmetric spectrum into a peak spectrum, and obtaining a residual spectrum by notching the peak spectrum. According to some embodiments, the guard components may be identified by selecting locations of a maximum spectral energy on both sides of the dominant component in the residual spectrum. According to other embodiments, the notching may include applying a symmetric averaging to the preprocessed signal by imposing a symmetric property around a dominant peak of the preprocessed signal and notching energy from the dominant component by removing the dominant component's influence on a nearby frequency range.

In certain embodiments, application of the symmetric averaging may include imposing a symmetric property around a dominant peak of the preprocessed signal. In some embodiments, the normalization may be applied using a moving window with a predefined length, and one sample in the vital signal may be normalized by removing a mean and a standard deviation in a sample centered time moving window. In other embodiments, the vital signal may be expressed as an amplitude and frequency modulation signal. In further embodiments, the time-frequency analysis may be performed and visualized using a periodogram.

Figure 9:
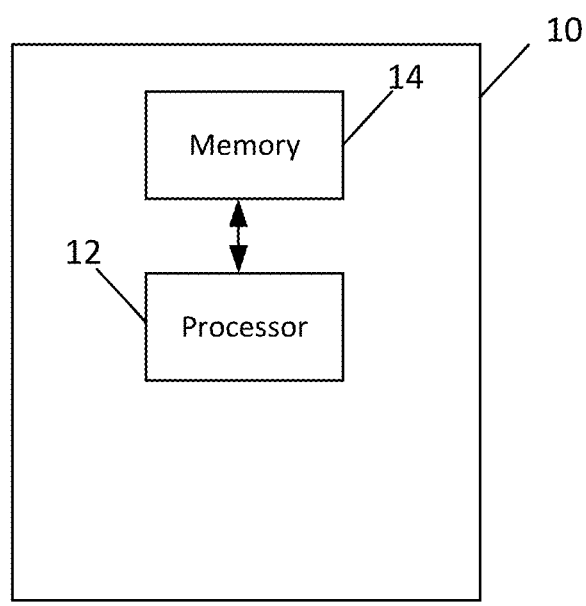
FIG. 9 illustrates an apparatus, according to certain embodiments.

FIG. 9 illustrates an apparatus 10 according to an example embodiment. In certain embodiments, although only one apparatus 10 is illustrated, apparatus 10 may be apparatus representing multiple apparatuses as part of a system or network. For example, in certain embodiments, apparatus 10 may be a PPG apparatus, wearable computer or communication device, mobile computer or communication device, or computer apparatus that operates individually or together in a computer system or computer network system.

In some embodiments, the functionality of any of the methods, processes, algorithms, or flow charts described herein may be implemented by software and/or computer program code or portions of code stored in memory or other computer-readable or tangible media and executed by a processor.

For example, in some embodiments, apparatus 10 may include one or more processors, one or more computer-readable storage mediums (for example, memory, storage, or the like), one or more radio access components (for example, a modem, a transceiver, or the like), and/or a user interface. It should be noted that one skilled in the art would understand that apparatus 10 may include components or features not shown in FIG. 9.

As illustrated in the example of FIG. 9, apparatus 10 may include or be coupled to a processor 12 for processing information and executing instructions or operations. Processor 12 may be any type of general or specific purpose processor. In fact, processor 12 may include one or more of general-purpose computers, special purpose computers, microprocessors, digital signal processors (DSPs), field-programmable gate arrays (FPGAs), application-specific integrated circuits (ASICs), and processors based on a multi-core processor architecture, as examples. While a single processor 12 is shown in FIG. 9, multiple processors may be utilized according to other embodiments. For example, it should be understood that, in certain example embodiments, apparatus 10 may include two or more processors that may form a multiprocessor system (e.g., in this case processor 12 may represent a multiprocessor) that may support multiprocessing. According to certain example embodiments, the multiprocessor system may be tightly coupled or loosely coupled (e.g., to form a computer cluster).

Processor 12 may perform functions associated with the operation of apparatus 10 including, as some examples, precoding of antenna gain/phase parameters, encoding and decoding of individual bits forming a communication message, formatting of information, and overall control of the apparatus 10, including processes illustrated in FIGS. 1-8.

Apparatus 10 may further include or be coupled to a memory 14 (internal or external), which may be coupled to processor 12, for storing information and instructions that may be executed by processor 12. Memory 14 may be one or more memories and of any type suitable to the local application environment, and may be implemented using any suitable volatile or nonvolatile data storage technology such as a semiconductor-based memory device, a magnetic memory device and system, an optical memory device and system, fixed memory, and/or removable memory. For example, memory 14 can be comprised of any combination of random access memory (RAM), read-only memory (ROM), static storage such as a magnetic or optical disk, hard disk drive (HDD), or any other type of non-transitory machine or computer-readable media. The instructions stored in memory 14 may include program instructions or computer program code that, when executed by processor 12, enable the apparatus 10 to perform any of the various tasks described herein.

In certain embodiments, apparatus 10 may further include or be coupled to (internal or external) a drive or port that is configured to accept and read an external computer-readable storage medium, such as an optical disc, USB drive, flash drive, or any other storage medium. For example, the external computer-readable storage medium may store a computer program or software for execution by processor 12 and/or apparatus 10 to perform any of the methods illustrated in FIGS. 1-8.

Additionally or alternatively, in some embodiments, apparatus 10 may include an input and/or output device (I/O device). In certain embodiments, apparatus 10 may further include a user interface, such as a graphical user interface or touchscreen.

In certain embodiments, memory 14 stores software modules that provide functionality when executed by processor 12. The modules may include, for example, an operating system that provides operating system functionality for apparatus 10. The memory may also store one or more functional modules, such as an application or program, to provide additional functionality for apparatus 10. The components of apparatus 10 may be implemented in hardware, or as any suitable combination of hardware and software. According to certain example embodiments, processor 12 and memory 14 may be included in or may form a part of processing circuitry or control circuitry.

As used herein, the term "circuitry" may refer to hardware-only circuitry implementations (e.g., analog and/or digital circuitry), combinations of hardware circuits and software, combinations of analog and/or digital hardware circuits with software/firmware, any portions of hardware processor(s) with software (including digital signal processors) that work together to cause an apparatus (e.g., apparatus 10) to perform various functions, and/or hardware circuit(s) and/or processor(s), or portions thereof, that use software for operation but where the software may not be present when it is not needed for operation. As a further example, as used herein, the term "circuitry" may also cover an implementation of merely a hardware circuit or processor (or multiple processors), or portion of a hardware circuit or processor, and its accompanying software and/or firmware.

According to certain embodiments, apparatus 10 may be controlled by memory 14 and processor 12 to receive a vital signal of a subject from a remote sensing device. Apparatus 10 may also be controlled by memory 14 and processor 12 to perform a preprocessing procedure on the vital signal via bandpass filtering and normalization to obtain a preprocessed signal. Apparatus 10 may further be controlled by memory 14 and processor 12 to perform a time-frequency analysis of the preprocessed signal. In addition, apparatus 10 may be controlled by memory 14 and processor 12 to estimate a HR of the subject from a dominant component of the preprocessed signal by finding the location of a maximum spectral energy of the time-frequency analysis. Further, apparatus 10 may be controlled by memory 14 and processor 12 to identify guard components in the preprocessed signal with respect to the dominant component. Apparatus 10 may also be controlled by memory 14 and processor 12 to derive a RR of the subject from a length of an interval between the dominant component and each of the guard components.

In some example embodiments, an apparatus (e.g., apparatus 10 and/or apparatus 20) may include means for performing a method, a process, or any of the variants discussed herein. Examples of the means may include one or more processors, memory, controllers, transmitters, receivers, and/or computer program code for causing the performance of the operations.

Certain example embodiments may be directed to an apparatus that includes means for receiving a vital signal of a subject from a remote sensing device. The apparatus may also include means for performing a preprocessing procedure on the vital signal via bandpass filtering and normalization to obtain a preprocessed signal. The apparatus may further include means for performing a time-frequency analysis of the preprocessed signal. In addition, the apparatus may include means for estimating a HR of the subject from a dominant component of the preprocessed signal by finding the location of a maximum spectral energy of the time-frequency analysis. Further, the apparatus may include means for identifying guard components in the preprocessed signal with respect to the dominant component. The apparatus may also include means for deriving a RR of the subject from a length of an interval between the dominant component and each of the guard components.

Certain embodiments described herein provide several technical improvements, enhancements, and/or advantages. In some embodiments, it may be possible to utilize an AM-FM to model PPG signals, which exploits two kinds of robust respiration-induced features of PPG signals: RIAV and RIFV. According to certain embodiments, the AM-FM model may be consistent with the observation of two guard components lying symmetrically around the dominant component in the PPG spectrum. Based on the model, it may be possible to develop a robust and efficient frequency-domain method to directly extract HR and RR from the PPG spectra. Additionally, the method of certain embodiments may be evaluated both on a contact-based PPG dataset collected by a pulse oximeter and on a remote PPG dataset including a set of face videos collected by a color camera. The extensive experimental results described herein demonstrate that the AM-FM method of certain embodiments is effective and robust even in relatively noisy scenarios of remote PPG data.

As discussed herein, to improve method robustness in the cPPG signal, the time-domain methods utilize all three respiratory-induced variation features in the signal, from which three individual RR estimates are extracted, but each time-domain approach fuses these estimates in a slightly different way to obtain the RR. In SmartFusion, averaging may be employed to provide a final estimate in each window, and the algorithm may discard the RR estimate if a large discrepancy exists among the three individual estimates. However, discarding data does not truly improve the RR estimation accuracy, but rather adds an unknown final estimate. On average, 35% of the windows in each case were eliminated due to disagreement in the three estimates. In ARFusion, the final estimate may be derived by fusing the AR spectra of the three respiratory-induced variations with several model orders. Although this fusing method is more advanced than average fusing, it still cannot avoid the peak/valley detection problem in a noisy spectrum. The p-value between SmartFusion and ARFusion (p=0.48) also shows that their performances have no significant difference in terms of RMSE.

The frequency-domain methods described herein, unlike the time-domain methods, only consider the RIIV in the PPG signal. They model the PPG signal as the superimposition of the pulse signal and the respiration signal. These methods typically analyze the PPG spectrum and extract HR and RR from different frequency ranges of interest. Different frequency analysis techniques such as periodogram, wavelet, EMD, EWT, and CSD are introduced in these algorithms to estimate the spectrum of the PPG signal. Given the assumption that the RR component is in a lower frequency range (0.1–0.7 Hz) and the HR component is in a higher frequency range (0.7–4 Hz), the HR and RR can be extracted from these ranges. Although advanced frequency analysis methods, such as EMD, EWT, and CSD, can help decompose the signal into different frequency sub-bands and improve the spectral estimation accuracy, these methods only consider RIIV in the PPG signal, which can be easily influenced by slow varying noise or removed by necessary preprocessing steps, such as de-trending and filtering. The relatively large variances of RMSE in the EMD, EWT, and CSD methods (FIG. 6) demonstrate the drawback of these methods based on the superimposition assumption. Moreover, the CSD method requires a sliding window of at least 60 seconds to obtain reliable RR estimates, resulting in a time delay in estimation.

Compared with RIIV, certain embodiments may focus on RIAV and RIFV that are more resistant to additive noise and preprocessing, analogous to the noise resistance of AM and FM in radio communication. In certain embodiments, by taking the effects of RIAV and RIFV into account, PPG signals can be modeled with amplitude and frequency modulation, rather than only considering RIIV, as the conventional frequency-domain methods do. VFCDM can be applied to extract AM and FM dynamics from a signal, but it is a general frequency analysis framework used to estimate variable frequency. The results show that VFCDM has a larger performance error than the method of certain embodiments described herein. Assuming the single-frequency modulation in AM and FM, certain embodiments may adapt and simplify the AM-FM model to meet the needs of RR estimation from PPG signals. The resulting AM-FM model explains the three noticeable components—a dominant component and its two guard components—in the PPG spectra. By taking advantage of the symmetric property of the three components, the algorithm of certain embodiments can successfully extract them from the PPG spectrum and obtain the HR and RR, while avoiding the potential problem(s) associated with peak/valley detection. The performance in Table 1 demonstrates that the AM-FM method of certain embodiments can estimate RR from the cPPG signal more accurately than other conventional methods.

Furthermore, the AM-FM method of certain embodiments may be computationally efficient. For example, the average processing time for 100 RR estimations is about 2 seconds with a single processor thread on a 2.4 GHz PC with 8 GB memory, performing real-time execution. The step of energy notching provided by certain embodiments solves a linear programming problem for each RR estimate, which takes a substantial percentage of the overall computational load.

Certain embodiments have also been tested in rPPG scenarios. In particular, the performance of the AM-FM method on rPPG signals have been tested, and the performance of the AM-FM method with the HRV, EMD, and EWT methods have been compared. rPPG is an emerging modality of PPG that has two main challenges in processing rPPG data. First, an rPPG signal has much lower SNR than a cPPG signal. The HRV-based methods extracted the RIFV signal from the rPPG signal to estimate the RR, since this kind of variation is a relatively robust feature in noisy scenarios. Due to a large amount of noise in the rPPG signal, it may be difficult for the time-domain methods to provide reliable detection of peaks and valleys, leading to large estimation errors. Second, the baseline shift of the rPPG signal coming from illumination variation from the external environment can weaken the RIIV effect on the signal. Thus, tests have been conducted on the rPPG signal EMD and EWT that are based on the RIIV effect, and Table 2 shows these two methods suffer from large error and variance. The above discussion suggests that the previous methods may not be applicable to the rPPG signal. In contrast, the proposed AM-FM method considers relatively robust RIAV and RIFV features, and extracts them robustly from the frequency domain, thus achieving better performance than the time-domain methods based on peak/valley detection algorithms and the frequency-domain methods that only consider RIIV features. Overall, the performance of the AM-FM method on the rPPG signal (Table 2) indicates that it improves the accuracy of RR estimation and is robust under noisy conditions.

Based on the analyzed breathing rate, the information can be displayed on a computer device or software application for users to guide their health management, monitor medical conditions related to breathing (e.g., chronic obstructive pulmonary disease (COPD), and other health/medical conditions). Certain embodiments may also promote safety and wellness including, but not limited to, for example, safe and wellness for drivers and machine operators.

A computer program product may include one or more computer-executable components which, when the program is run, are configured to carry out some example embodiments. The one or more computer-executable components may be at least one software code or portions of it. Modifications and configurations required for implementing operations of certain example embodiments may be performed as routine(s), which may be implemented as added or updated software routine(s). Software routine(s) may be downloaded into the apparatus.

As an example, software or a computer program code or portions of it may be in a source code form, object code form, or in some intermediate form, and it may be stored in some sort of carrier, distribution medium, or computer-readable medium, which may be any entity or device capable of carrying the program. Such carriers may include a record medium, computer memory, read-only memory, photoelectrical and/or electrical carrier signal, telecommunications signal, and software distribution package, for example. Depending on the processing power needed, the computer program may be executed in a single electronic digital computer or it may be distributed amongst a number of computers. The computer-readable medium or computer-readable storage medium may be a non-transitory medium.

In other example embodiments, the functionality may be performed by hardware or circuitry included in an apparatus (e.g., apparatus 10 or apparatus 20), for example through the use of an application-specific integrated circuit (ASIC), a programmable gate array (PGA), a field-programmable gate array (FPGA), or any other combination of hardware and software. In yet another example embodiment, the functionality may be implemented as a signal, a non-tangible means that can be carried by an electromagnetic signal downloaded from the Internet or other network.

According to an example embodiment, an apparatus, such as a device, or a corresponding component, may be configured as circuitry, a computer or a microprocessor, such as a single-chip computer element, or as a chipset, including at least a memory for providing storage capacity used for arithmetic operation and an operation processor for executing the arithmetic operation.

One having skill in the art will readily understand that the description as discussed above may be practiced with procedures in a different order, and/or with hardware elements in configurations, which are different than those which are disclosed. Therefore, although the present disclosure presents and describes certain example embodiments, it would be apparent to those of skill in the art that certain modifications, variations, and alternative constructions would be apparent while remaining within the spirit and scope of example embodiments.

PARTIAL GLOSSARY

AM Amplitude Modulation
FM Frequency Modulation
BrPM Breaths per Minute
HR Heart Rate
PPG Photoplethysmography
RIAV Respiratory-Induced Amplitude Variation
RIFV Respiratory-Induced Frequency Variation
RIIV Respiratory-Induced Intensity Variation
RMSE Root Mean Square Error
RR Respiratory Rate

We claim:

1. An apparatus for vital sign extraction, comprising:
at least one processor;
and at least one memory comprising computer program code,
the at least one memory and the computer program code are configured, with the at least one processor, to cause the apparatus at least to
receive a photoplethysmography signal of a subject from a sensing device;
perform a preprocessing procedure on the photoplethysmography signal via bandpass filtering and normalization to obtain a preprocessed signal;
perform a time-frequency analysis of the preprocessed signal;
estimate a heart rate of the subject from a dominant frequency trace of the preprocessed signal by finding location of a maximum spectral energy of the time-frequency analysis;
apply a symmetric averaging to the preprocessed signal by flipping a spectrum around the dominant frequency trace to generate a symmetric spectrum;
decompose the symmetric spectrum into a peak spectrum;
generate a residual spectrum by notching the peak spectrum, wherein the notching comprises estimating a shape of the dominate frequency trace, and subtracting the shape of the dominant frequency trace from an original photoplethysmography spectrum;
identify, from the residual spectrum, guard frequency traces in the preprocessed signal with respect to the dominant frequency trace;
derive a respiratory rate of the subject from a length of an interval between the dominant component and each of the guard components; and
output the respiratory rate of the subject to a display on a computer device, or feed the dominant frequency trace and the guard frequency traces into an adaptive multi-trace carving module to track these frequency traces on spectrograms.

2. The apparatus for vital sign extraction according to claim 1, wherein the guard frequency traces are identified by selecting locations of a maximum spectral energy on both sides of the dominant frequency trace in the residual spectrum.

3. The apparatus for vital sign extraction according to claim 1,
wherein the normalization is applied using a moving window with a predefined length, and
wherein one sample in the photoplethysmography signal is normalized by removing a mean and a standard deviation in a sample centered time moving window.

4. The apparatus for vital sign extraction according to claim 1, wherein the time-frequency analysis is performed and visualized using a periodogram.

5. A method for vital sign extraction, comprising:
receiving a photoplethysmography signal of a subject from a remote sensing device;
performing a preprocessing procedure on the photoplethysmography signal via bandpass filtering and normalization to obtain a preprocessed signal;
performing a time-frequency analysis of the preprocessed signal;
estimating a heart rate of the subject from a dominant frequency trace of the preprocessed signal by finding location of a maximum spectral energy of the time-frequency analysis;
applying a symmetric averaging to the preprocessed signal by flipping a spectrum around the dominant frequency trace to generate a symmetric spectrum;
decomposing the symmetric spectrum into a peak spectrum;
generating a residual spectrum by notching the peak spectrum, wherein the notching comprises estimating a shape of the dominate frequency trace, and subtracting the shape of the dominant frequency trace from an original photoplethysmography spectrum;
identifying, from the residual spectrum, guard frequency traces in the preprocessed signal with respect to the dominant frequency trace;
deriving a respiratory rate of the subject from a length of an interval between the dominant component and each of the guard components; and
outputting the respiratory rate of the subject to a display on a computer device, or feeding the dominant frequency trace and the guard frequency traces into an adaptive multi-trace carving module to track these frequency traces on spectrograms.

6. The method for vital sign extraction according to claim 5, wherein the guard frequency traces are identified by selecting locations of a maximum spectral energy on both sides of the dominant frequency trace in the residual spectrum.

7. The method for vital sign extraction according to claim 5,
wherein the normalization is applied using a moving window with a predefined length, and
wherein one sample in the photoplethysmography signal is normalized by removing a mean and a standard deviation in a sample centered time moving window.

8. The method for vital sign extraction according to claim 5, wherein the time-frequency analysis is performed and visualized using a periodogram.

9. A non-transitory computer readable medium encoded with instructions that, when executed in hardware, perform a process, the process comprising;
receiving a photoplethysmography signal of a subject from a remote sensing device;
performing a preprocessing procedure on the photoplethysmography signal via bandpass filtering and normalization to obtain a preprocessed signal;

performing a time-frequency analysis of the preprocessed signal;

estimating a heart rate of the subject from a dominant frequency trace of the preprocessed signal by finding location of a maximum spectral energy of the time-frequency analysis;

applying a symmetric averaging to the preprocessed signal by flipping a spectrum around the dominant frequency trace to generate a symmetric spectrum;

decomposing the symmetric spectrum into a peak spectrum;

generating a residual spectrum by notching the peak spectrum, wherein the notching comprises estimating a shape of the dominate frequency trace, and subtracting the shape of the dominant frequency trace from an original photoplethysmography spectrum;

identifying, from the residual spectrum, guard frequency traces in the preprocessed signal with respect to the dominant frequency trace;

deriving a respiratory rate of the subject from a length of an interval between the dominant component and each of the guard components; and outputting the respiratory rate of the subject to a display on a computer device, or feeding the dominant frequency trace and the guard frequency traces into an adaptive multi-trace carving module to track these frequency traces on spectrograms.

10. The non-transitory computer readable medium according to claim 9, wherein the guard frequency traces are identified by selecting locations of a maximum spectral energy on both sides of the dominant frequency trace in the residual spectrum.

11. The non-transitory computer readable medium according to claim 9, wherein the normalization is applied using a moving window with a length of one second, and wherein one sample in the photoplethysmography signal is normalized by removing a mean and a standard deviation in a sample centered time moving window.

* * * * *